(12) United States Patent
Volland

(10) Patent No.: US 11,396,011 B2
(45) Date of Patent: Jul. 26, 2022

(54) DEVICE FOR TAKING A SAMPLE AND SAMPLE ANALYSIS SYSTEM COMPRISING SUCH A DEVICE

(71) Applicant: COMMISSARIAT A L'ENERGIE ATOMIQUE ET AUX ENERGIES ALTERNATIVES, Paris (FR)

(72) Inventor: Herve Volland, Orsay (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 264 days.

(21) Appl. No.: 16/341,522

(22) PCT Filed: Oct. 23, 2017

(86) PCT No.: PCT/FR2017/052913
§ 371 (c)(1),
(2) Date: Apr. 12, 2019

(87) PCT Pub. No.: WO2018/078266
PCT Pub. Date: May 3, 2018

(65) Prior Publication Data
US 2019/0366326 A1    Dec. 5, 2019

(30) Foreign Application Priority Data
Oct. 24, 2016    (FR) ..................................... 16 60289

(51) Int. Cl.
*G01N 21/78*    (2006.01)
*G01N 1/02*    (2006.01)
(Continued)

(52) U.S. Cl.
CPC ................ *B01L 3/502* (2013.01); *G01N 1/10* (2013.01); *B01L 2200/026* (2013.01);
(Continued)

(58) Field of Classification Search
CPC ............... B01L 3/502; B01L 2200/026; B01L 2200/0631; B01L 2200/0689;
(Continued)

(56) References Cited

U.S. PATENT DOCUMENTS 4,180,383 A    12/1979  Johnson
4,580,577 A     4/1986  O'Brien et al.
(Continued)

FOREIGN PATENT DOCUMENTS

WO    WO 95/08761 A1    3/1995
WO    WO-0190297 A1 *  11/2001 ......... A61B 10/0291
(Continued)

OTHER PUBLICATIONS

International Search Report dated Mar. 2, 2018 in PCT/FR2017/052913 filed on Oct. 23, 2017.
(Continued)

*Primary Examiner* — Matthew D Krcha
*Assistant Examiner* — Sophia Y Lyle
(74) *Attorney, Agent, or Firm* — Oblon, McClelland, Maier & Neustadt, L.L.P.

(57)    ABSTRACT

A device for taking and optionally processing a sample, includes (i) a housing containing a porous matrix that can receive the sample, (ii) a stopper that can be connected to the housing in a tight manner and including a piston that ensures the tight closing of the housing, compressing the porous matrix or the sample, and (iii) a storage receptacle that can be connected to the housing, can receive the sample that has passed through the porous matrix, and includes at least one conduit connecting the inside of the receptacle to the outside, once the porous matrix or the sample is compressed. The device also includes a seal between the stopper and the storage receptacle. The stopper closes the storage receptacle
(Continued)

in a tight manner when the stopper and the storage receptacle are connected to the housing.

19 Claims, 5 Drawing Sheets

(51) Int. Cl.
*B01L 3/00* (2006.01)
*G01N 1/10* (2006.01)

(52) U.S. Cl.
CPC ............ *B01L 2200/0631* (2013.01); *B01L 2200/0689* (2013.01); *B01L 2200/16* (2013.01); *B01L 2300/025* (2013.01); *B01L 2300/042* (2013.01); *B01L 2300/044* (2013.01); *B01L 2300/0672* (2013.01); *B01L 2300/0681* (2013.01); *B01L 2300/0816* (2013.01); *B01L 2300/0825* (2013.01); *B01L 2300/0877* (2013.01); *B01L 2400/0478* (2013.01)

(58) Field of Classification Search
CPC .......... B01L 2200/16; B01L 2300/025; B01L 2300/042; B01L 2300/044; B01L 2300/0672; B01L 2300/0681; B01L 2300/0816; B01L 2300/0825; B01L 2300/0877; B01L 2400/0478; B01L 2300/0887; B01L 2300/069; B01L 2300/0832; B01L 3/5023; G01N 1/10; G01N 1/02; A61B 2010/0216; A61B 10/02; A61B 10/0045
See application file for complete search history.

(56) References Cited

U.S. PATENT DOCUMENTS

| | | |
|---|---|---|
| 5,211,182 A | 5/1993 | Deutsch et al. |
| 5,352,410 A | 10/1994 | Hansen et al. |
| 5,523,055 A | 6/1996 | Hansen et al. |
| 2001/0008614 A1 | 7/2001 | Aronowitz |
| 2002/0001822 A1* | 1/2002 | DiCesare ............... B01L 3/5029 435/40.5 |
| 2003/0177849 A1* | 9/2003 | Matsuda ............... B01L 3/0279 73/864.14 |
| 2005/0119589 A1 | 6/2005 | Tung et al. |
| 2005/0180882 A1* | 8/2005 | Tung ................. G01N 33/48714 422/504 |
| 2005/0202568 A1 | 9/2005 | Tung et al. |
| 2007/0128070 A1* | 6/2007 | Wu ....................... G01N 33/558 422/400 |
| 2008/0318342 A1* | 12/2008 | Durack ............ G01N 33/54386 436/526 |
| 2009/0117665 A1 | 5/2009 | Tung et al. |
| 2010/0089181 A1 | 4/2010 | Aronowitz |
| 2013/0158431 A1 | 6/2013 | Aronowitz |
| 2016/0121322 A1 | 5/2016 | Fuller et al. |
| 2016/0199834 A1* | 7/2016 | Bransky ............ B01L 3/502715 435/309.1 |

FOREIGN PATENT DOCUMENTS

| | | |
|---|---|---|
| WO | WO 2008/030817 A2 | 3/2008 |
| WO | WO 2009/036168 A2 | 3/2009 |
| WO | WO 2009/153559 A1 | 12/2009 |
| WO | WO 2012/118392 A1 | 9/2012 |

OTHER PUBLICATIONS

French Preliminary Search Report dated Jul. 7, 2017 in French Application 16 60289 filed on Oct. 24, 2016.

* cited by examiner

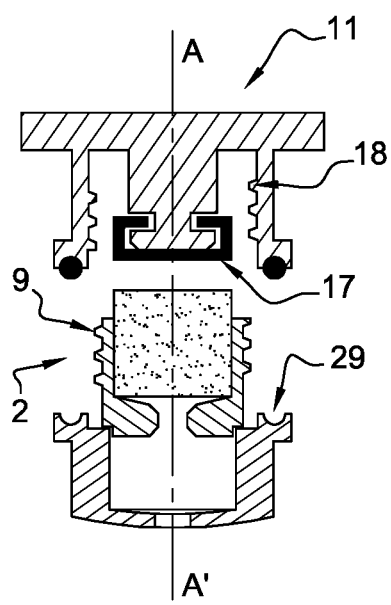
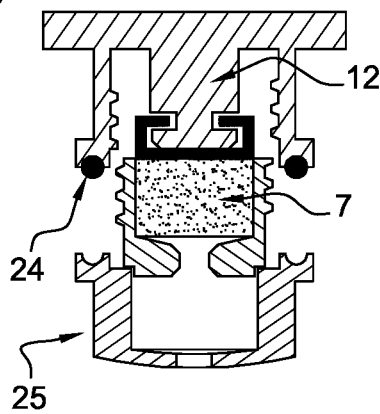
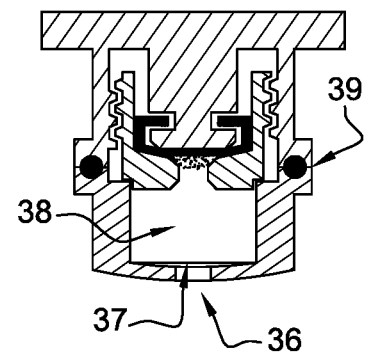
Fig. 4A          Fig. 4B          Fig. 4C
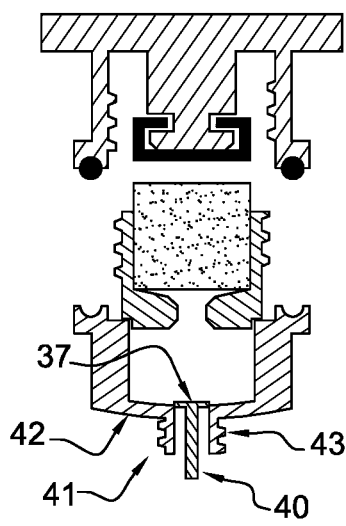
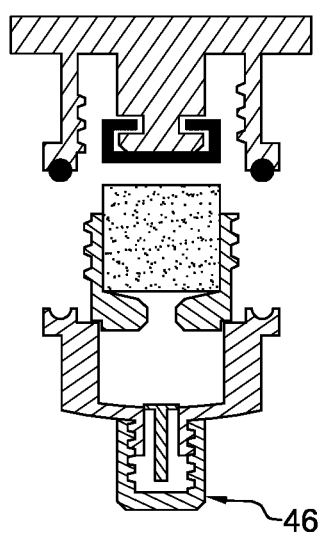
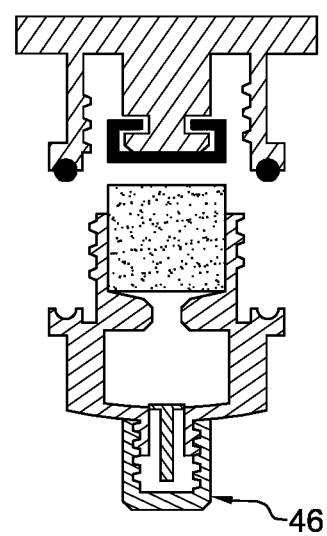
Fig. 5A          Fig. 5B          Fig. 5C

DEVICE FOR TAKING A SAMPLE AND SAMPLE ANALYSIS SYSTEM COMPRISING SUCH A DEVICE

TECHNICAL FIELD

The present invention relates to the technical field of devices for collecting and transporting samples and in particular liquid or surface samples.

Indeed, the present invention provides a device with three modules mechanically and/or fluidly connectable to each other thanks to which the sample is collected, treated and preserved with a minimum of user manipulations. Advantageously, these manipulations just consist in a sampling such as a pipetting or rubbing followed by simple operations such as screwing, clipping or drawing/stamping. Once the sample is collected, the device according to the invention enables, in a direct and simple way, that is without further manipulation of the sample, either the sample to be immediately analysed after a possible treatment, or the optionally treated sample to be sealingly preserved, for the subsequent analysis thereof.

The present invention relates to a system for analysing a sample comprising such a device and a strip cassette system adaptable to the device enabling the analyte(s) of interest present in the sample to be detected/quantified without further pipetting. This analysis system thus enables the operator to perform, with the same equipment, all the necessary operations, and in the required order, to obtain or display the result of determining the presence of the analyte(s) of interest, from the medium likely to contain it or them.

STATE OF PRIOR ART

Many works and studies in fields encompassing in particular academic research; clinical and diagnostic research and analyses, with tests made on blood samples or cell or tissue biopsies; environmental monitoring; civil monitoring; food security and in particular quality control; crime analyses on traces . . . involve collecting samples for the analysis thereof.

The state of the art knows several patents and patent applications already providing devices adapted to collect and store samples. By way of particular examples, International application WO 2012/118392 [1] and International application WO 2008/030817 [2] can be mentioned.

More particularly, the device subject-matter of the International application WO 2012/118392 [1] consists of a receptacle with a plug having a pierceable zone and that can have a rod with a sponge or pad type solid matrix. The receptacle has a rounded or conical bottom with one or more hole(s). The bottom of the receptacle is linked to a collector via a screw pitch or protrusions. In this application, the sample is taken using the rod attached to the plug; and then, the plug is screwed to the receptacle and a solution for diluting the sample is introduced through the pierceable zone. After stirring, the solution containing the sample is transferred into the collector by centrifugation. In other words, the use of a centrifuge is unavoidable to recover the sample, making the device incompatible with a use on site. In addition, the transfer of the sample for a subsequent analysis requires an additional manipulation such as a pipetting.

The device subject-matter of the International application WO 2008/030817 [2] has an enclosure in which a sponge or pad type solid matrix linked to a piston is located. Once this matrix is impregnated with the sample by capillarity, the enclosure is connected to a collector and the sample passes into the collector by manually compressing the matrix. The collector can be disconnected from the enclosure before being occluded by a plug in order to store the sample for a subsequent analysis thereof. This disconnection is however not without any risk of sample contamination or loss.

Subsequent analyses made on samples taken/collected and optionally stored aim at detecting the presence or absence of a particular analyte in the latter. These analyses can implement immunological sensors in the form of strips, commonly used for detecting many biological parameters but also to enable pathogenic agents to be detected.

Such a sensor also called a strip test is a detection system which is simple with a very small number of manipulations to make; quick, the result being obtained within 30 min; cheap and can be used on site by non-specialists. The strips are formed by 3 zones attached together on a plastic support, with (i) an absorption zone promoting migration, (ii) a reaction zone, generally formed by a nitrocellulose membrane and (iii) a deposition zone receiving the sample.

A last zone on which the "tracer" antibody has been deposited and dried is often associated to the latter. This antibody specifically directed against the analyte of interest is linked to molecules enabling a signal, generally a colorimetric or fluorescent signal, to be obtained.

Two lines of antibodies are deposited on the nitrocellulose membrane. The first of these lines called a "test" line is made by depositing antibodies specific to the analyte of interest (capture antibodies). It is the signal obtained at this line that will indicate the presence or not of the analyte of interest to be detected. In some cases, this signal also allows assaying. The second line called a "control" line generally consists of antibodies directed against the tracer antibody.

Upon making the test, if the analyte of interest is present in the sample, this will be recognised by the tracer antibody present at the deposition zone. The complex thus formed will be captured by the second antibody specific to the analyte of interest at the test line during migration. The excess tracer antibody that did not react with the analyte of interest will be in turn captured at the control line by the anti-tracer antibody antibody. If the analyte of interest is absent of the sample, no tracer antibody/analyte of interest complex will be formed and, consequently, the tracer antibody will not be immobilised at the test line. In this format, the test is thus positive if a signal appears at both lines and is negative if a signal only appears at the control line. If, at the end of the test, no signal appears, even at the control line, that means that the test has not been performed under proper conditions or that the sample is not analysable as such.

The state of the art also knows devices associating taking/collecting and analysis as, for example, via strip tests.

For example, International application WO 95/08761 [3] provides a device comprised of a hollow structure inside which an absorbing wick/pad is placed. One of the ends of this structure enables the wick to exit. At the opposite end, the system for analysing the sample is located. To take the sample, the wick exits this structure and absorbs the liquid sample. For the analysis, the wick is contacted with the analysis system. It is noted that the device described in [3] does not have a tank which enables the sample to be stored and transported or even analysed in a delayed manner.

International application WO 2009/036168 [4] describes a device for taking, analysing and storing a sample. This device has, on the one hand, a pad/sponge which enables liquid, surface and air samples to be taken and, on the other hand, a tank containing a buffer solution which enables the pad/sponge to be washed and thus the sample to be recovered after the housing of the pad/sponge is closed. Initiating the washing is made by the manipulator. The sample is then analysed by a test (example a strip) contained in the device. Even if the device described in [4] seems to be simple to use, its manufacture requires assembling many parts some of which should be movable. The production of such a device is thus complicated and expensive.

International application WO 2009/153559 [5] describes a device consisting of a female part in which an absorbent is inserted and a male part which can be inserted into the female part. At the end of the female part opposite to that for inserting the male part, a communication is possible to the outside. A detection system is located at this end and analyses the sample from the female part. The surface sample is taken thanks to the wetted absorbent and then the sample is transferred to the detection system, either by compressing the absorbent using the male part, or by sucking from the side opposite to the male part. Once again, the device of [5] does not have a tank which enables the sample to be stored and transported or even analysed in a delayed manner.

Finally, the device subject-matter of the patent application US 2016/121322 [6] comprises a body provided with (i) a sponge able to absorb an oral fluidic sample, (ii) a strip able to receive said sample and (iii) a portion defining a fluidic tank and a channel in which the strip is located. This device further has a capsule able to partially cover the body by means of pressing/rotating and comprising a fluidic tank containing a fluid for being mixed to the sample. However, a prolonged storage of the sample in such a device does not appear possible.

The inventors have set the purpose of providing a device which is simple of use, cheap as regards its manufacture and enabling, on the one hand, samples to be readily taken regardless of whether they are liquid or surface samples and, on the other hand, the samples to be transported and stored for a future analysis.

The inventors have also set the purpose of providing a device which is readily adaptable on analysis systems such as a strip tests, in order to have available a tool enabling all the steps from taking to rendering the results to be readily made (without requiring many user manipulations).

The inventors have also set the purpose of providing a device the characteristics of which enable several analytes of interest to be tested at the same time and to ensure improved test performance with respect to the results obtained on analysis systems such as conventional strip tests.

DISCLOSURE OF THE INVENTION

The present invention enables the purposes set by the inventors to be achieved and to solve all or part of the technical problems of the taking/collecting devices of prior art.

Indeed, the present inventors have developed a device which is simple to use and does not require a particular knowledge to that end. This device has three modules, connectable to each other, with a plug/piston, a taking module and a tank, said device facilitating taking a liquid or surface sample. This device enables the sample to be stored in a hermetically closed volume implying the plug/piston, the taking module and the tank. In addition, the treatment of the sample and in particular its incubation with a molecule that can be bound to the analyte and producing a measurable signal are allowed and facilitated. The different functions of this device facilitate the sample manipulation and optionally enable the signals of the detection tests to be increased.

In particular, the porous, optionally compressible, matrix, present in the device according to the invention enables a liquid sample or a sample on a solid surface to be collected. The possibility of an incubation between the analyte present in the sample and a labelled molecule that birds to the analyte in the taking device or the tank promote interaction between both elements and the storage ability enables the sample analysis to be made when and where needed.

Finally, this device simplifies depositing the sample onto a detection/quantification system such as strip tests, a hermetic connection between this device and the cassette containing one or more reactive strip(s) enabling a simplified and secured deposition to be ensured.

Thus, the present invention relates to a device for taking and optionally processing a sample, said device comprising:

an enclosure/housing with a first open end and a second end having a hole, a porous matrix, disposed in said enclosure and able to recover said sample, a plug/stopper connectable to said first end of said enclosure and having a piston sealingly closing said first end of said enclosure, said plug being movable with respect to said enclosure from an initial position to a final position whereby said piston compresses said porous matrix or said sample, a tank/storage receptacle connectable to said second end of said enclosure and in fluid connection with said enclosure via said hole so as to recover the sample restored by said porous matrix under the effect of the compression of said porous matrix or said sample by said piston, said tank having one or more conduit(s) connecting the inner volume of the tank to the outside, sealing means being present between said plug and said tank and when said plug and said tank are connected to said enclosure and when said plug is in said final position, said plug sealingly closing said tank.

The device according to the present invention thus comprises three modules interacting with each other by means of mechanical and/or fluidic connections.

The first of these modules is the central module participating in collecting and/or taking the sample: it comprises an enclosure and a porous, compressible or not compressible, matrix placed in this enclosure. The terms "first module", "taking module" and "sampler" are equivalent and usable interchangeably in the present invention.

Typically, this enclosure is in a circular cross-section tubular cylindrical form with a first open end and a second end having a hole, said ends being positioned facing each other.

The second end of this enclosure may only have one through hole or, otherwise, have several holes and in particular two, three, four or a plurality of through holes evenly or not evenly distributed at the second end. In a particular embodiment, the hole can have an internal diameter identical or substantially identical to the internal diameter of the second end of the enclosure. Such an embodiment is in particular implemented when the porous matrix is a filtration membrane.

Within the scope of the present invention, the porous, compressible or not compressible, matrix implemented can be any solid support able, on the one hand, to absorb and/or filter a sample and, on the other hand, to restore this sample in response to a compression of said matrix when it is porous or of the liquid sample when the porous matrix is not compressible. This matrix is a solid support having pores which have a regular or an irregular size and are randomly distributed. This matrix is typically in the form of a sponge, a foam, a pad, when it is compressible or in the form of a filtration membrane, when it is not compressible. This matrix is advantageously of a material comprising cellulose, cellulose esters, polyvinylidene fluoride (PVDF), nitrocellulose, polycarbonate, an elastomer or a mixture thereof. Those skilled in the art will be able to determine, without inventive effort, the most suitable material for the porous matrix and its compressible or not compressible nature (foam or filter) as a function of the nature and in particular the hydrophilic or hydrophobic character of the sample to be taken.

Typically, the porous matrix has a circular cross-section solid cylindrical shape. Advantageously, the diameter of the porous matrix is identical or substantially identical to the internal diameter of the tubular cylindrical shaped enclosure such that the sample does not miss said matrix to join the tank. In other words, there is a direct contact between the inner sidewall of the enclosure and the porous matrix.

When the matrix is porous and compressible, before the plug is connected to the open end of the enclosure, the matrix can project i.e. emerge from the open end of the enclosure in order to facilitate direct taking of the sample.

In a first embodiment, the sample to be taken is a liquid sample. By "liquid sample", it is meant any natural or synthetic, hydrophilic or hydrophobic solution, desired to be taken by means of the device of the invention.

Thus, this liquid sample can be a biological fluid; a plant fluid such as sap, nectar and root exudate; a sample in a culture medium or in a biological culture reactor such as a cell culture of higher eukaryotes, of yeasts, of fungi or of algae; a liquid obtained from one (or more) animal or plant cell(s); a liquid obtained from an animal or plant tissue; a taking in a food matrix; a taking in a chemical reactor; municipal, river, pond, lake, sea, or air-cooled tower water; a taking from a liquid industrial effluent; waste water coming in particular from intensive animal production or industries of the chemical, pharmaceutical, cosmetic or nuclear field; a pharmaceutical product; a cosmetic product; a fragrance; a soil sample or a mixture thereof.

When the liquid sample is a biological fluid, the latter is advantageously chosen from the group consisting of blood such as whole blood or anti-coagulated whole blood, blood serum, blood plasma, lymph, saliva, sputum, tears, sweat, sperm, urine, faeces, milk, cerebrospinal fluid, interstitial fluid, an isolated bone marrow fluid, a respiratory tract, intestinal or genito-urinary mucus or fluid, cellular extracts, tissue extracts and organ extracts. Thus, the biological fluid can be any fluid naturally secreted or excreted from a human or animal body or any fluid recovered, from a human or animal body, by any technique known to those skilled in the art such as extraction, taking or washing. The steps of recovering and isolating these different fluids from the human or animal body are made prior to contacting with the device according to the present invention.

Likewise, if one of the contemplated samples does not allow taking using the device according to the present invention, for example because of its nature being in particular solid, its concentration or elements it contains such as solid residues, waste, suspension or interfering molecules, the taking such as defined hereinafter further comprises a prior step of preparing the sample with optionally solubilising the sample by techniques known to those skilled in the art such as filtration, precipitation, dilution, distillation, mixing, concentration, lysis, etc. Alternatively, such steps can be implemented using the device according to the invention as explained hereinafter.

When the sample to be taken is a liquid sample and the porous matrix is compressible, the taking can consist in depositing, on the same, the sample. Typically, the sample is deposited onto the porous matrix and compressible by pipetting. Alternatively, the matrix can be contacted with the liquid sample such that the latter is absorbed by capillarity by the matrix. When the porous matrix is not compressible and is, for example, in the form of a filtration membrane, the sample is deposited into the enclosure containing or not a solution such as culture medium or an extraction buffer. This liquid sample can come from solubilising a solid sample, as, for example, a sample collected by means of a swab.

In a second embodiment, the sample to be taken is a surface sample. By "surface sample", it is meant a sample obtained from a set of organic compounds and/or inorganic compounds present at the surface of a support and being initially in dry or substantially dry form.

When the sample to be taken is a surface sample, the taking implements a porous compressible matrix and first consists in soaking the latter with an adapted buffer either by depositing/pipetting, or by capillarity absorption and then rubbing the surface of the support concerned with the porous matrix thus soaked.

The second module of the device according to the invention corresponds to the plug/piston which enables, when connected to the enclosure of the first module, at the open end thereof, the porous matrix or the sample contained in the enclosure to be compressed whereby the sample is extracted from the porous matrix and passes into the inner volume of the tank, i.e. the third module. The terms "second module", "plug/piston module" and "plug/piston" are equivalent and usable interchangeably in the present invention.

In a first embodiment, the sample passes from the enclosure to the tank thanks to the compression of the porous compressible matrix by the piston, resulting from the movement of the plug with respect to the enclosure from an initial position to a final position. By "initial position", it is meant the position of the plug when the latter contacts with the open end of the enclosure. By "final position", it is meant the position in which the movement of the plug with respect to the enclosure is maximum. When the plug is moved with respect to the enclosure, the piston slides inside the enclosure. It is to be noted that the porous matrix is not attached to the piston.

In a second embodiment, the porous matrix is not compressible, and it is the liquid or suspended sample present in the enclosure which is compressed or pushed by the piston, when the plug moves with respect to the enclosure from an initial position to a final position.

Typically, the piston is in the form of a single circular cross-section closed cylinder, mounted or attached to the plug. In this implementation form, the diameter of the piston is identical to the internal diameter of the tubular cylindrical shaped enclosure of the first module. Alternatively, the piston can have a diameter lower than the internal diameter of the enclosure. In this case, however, the piston head in contact with the porous matrix has a seal. The latter can extend circumferentially about the piston head and/or covering this head. Whatever the arrangement of this seal, it has an external diameter identical or even higher than the internal diameter of the enclosure. A seal can also be used when the diameter of the piston is identical to the internal diameter of the enclosure. In all the alternatives contemplated above, the piston ensures a sealed closure of the first end of the enclosure.

Any means for removably connecting the plug to the first end of the enclosure can be used within the scope of the present invention. By way of illustrating examples, this connection can involve screwing, clipping, notching, ribbing and/or a bayonet attachment. In one advantageous embodiment, this connection is made by screwing and the plug is connectable to the first end of the enclosure by means of threads. In this embodiment, the piston and the plug have the same axis of rotation. Thus, screwing the plug to the first end of the enclosure causes the compression of the porous matrix or the liquid sample contained in the enclosure by said piston.

The third module of the device according to the invention corresponds to the tank which, when connected to the enclosure of the first module, at the second end of the same, recovers the sample after the latter passes through the porous matrix. To perform this recovery, the tank is in fluid connection with the enclosure via the hole of the second end thereof.

The terms "third module", "tank module" and "tank" are equivalent and interchangeably usable in the present invention.

Within the scope of the present invention, the tank can have any shape allowing a hermetic connection to the enclosure of the first module, at the second end thereof. Typically, this tank is of a cylindrical shape with a first open end. This first open end directly participates in connecting the enclosure by screwing, clipping, notching, ribbing and/or bayonet attachment. The external diameter of the tank can be lower than, identical or higher than the external diameter of the enclosure. In a particular embodiment, the external diameter of the tank is higher than the external diameter of the enclosure.

One of the features of the device according to the present invention is in the fact that, when the plug is connected to the enclosure and is in the final position as previously defined and when the tank is connected to the enclosure, the plug closes or encloses or engages the tank, in a sealed manner. Advantageously, the plug is in direct contact with the tank, sealing means existing between the plug and the tank. In this organisation, the plug and the tank sealingly close the device whereby the latter and the sample it contains can be preserved or stored, in a secured way. In particular, in this embodiment, that is when the plug is connected to the enclosure and is in the final position as previously defined and when the tank is connected to the enclosure, the plug and the tank form a single sealed closed volume which contains the enclosure, i.e. the first module. It is possible to further enhance sealing of the volume thus formed and avoid a detrimental opening of the device by having at the joint between the plug and the tank an adhesive tape and in particular a friable adhesive tape.

Any sealing means known to those skilled in the art can be implemented between the plug and the tank. In a particular embodiment, these sealing means involve a seal, and the latter can be carried either by the tank, or by the plug. In one particular embodiment, these sealing means are in the form of a seal carried by the plug. In this case, the tank has a cavity or throat in which the seal can be sealingly housed. Alternatively, the tank has an annular housing to which the seal can be sealingly wedged. Typically, the seal implemented within the scope of the present invention is an O-ring or a lip seal.

Any means for removably or irremovably connecting the tank to the second end of the enclosure is usable within the scope of the present invention. Indeed, it is possible, upon taking and treating the sample, to replace a first tank with a second tank, as illustrated in the example IV.2.a hereinafter. By way of illustrating examples, this connection can involve adhering, drawing/stamping, screwing, clipping, notching, ribbing and/or bayonet attachment. Thus, this connection implements one or more notch(es), one or more projection(s), one or more lug(s), one or more protrusion(s), one or more tab(s) and one or more recess(es) at the second end of the enclosure and the first end of the tank. In an alternative of irremovable connection of the tank to the second end of the enclosure, the tank and the enclosure can form a single structure.

The tank of the device according to the invention has also one or more conduit(s) connecting the inner volume of the tank to the outside. In this way, any overpressure risk in the inner volume of the tank is avoided upon compressing the porous matrix or the sample by moving the plug with respect to the enclosure from an initial position to a final position as previously defined. Advantageously, when the plug and the tank are connected to the enclosure and when the plug is in the final position, this(these) conduit(s) is (are) occluded, thus ensuring sealing of the device according to the present invention.

Advantageously, in the device according to the invention, the tank further has an occludable hole. In the non-occluded state, this hole makes it possible that whole or part of the sample is extracted from the tank for the purpose of removal or analysis. Otherwise, when this hole is occluded, the sample is held in the tank, which is in particular the case upon storing or transporting the sample in the device according to the present invention.

This occludable hole is at the end facing the first open end of the tank. This second end of the tank may have only one occludable hole or, otherwise, have several holes and in particular two, three, four or a plurality of occludable holes evenly or not evenly distributed, at the second end.

The tank of the device according to the invention thus has means for occluding the hole(s), in a removable or breakable manner. These means can be at the inner or outer wall of the tank or even can pass through the occludable hole(s). Typically, means for occluding an occludable hole are in the form of an occluder and in particular of an occluder coupled to a spike removably disposed in this hole.

Advantageously, the device according to the invention further has a hole occludable by a removable occluder. In one particular embodiment, the hole occludable by a removable occluder, present at the tank is protected by a plug, whereby no inadvertent opening of this hole will occur. Indeed, the user will have to perform the unscrewing of the protective plug before the occluded hole can be open.

In order to treat the sample during taking or storing the same, the device according to the invention can further comprise at least one element able to physically or chemically process/treat this sample.

In a particular embodiment, this element is a filtration membrane. The latter enables elements such as cells present in the sample to be separated, isolated or even extracted from the rest of the sample. This filtration membrane can be placed in the enclosure between the compressible porous matrix and the second end of this enclosure.

In another embodiment, this element is a chemical reagent. By way of examples of such reagents, a dilution buffer, a lysis buffer, a washing buffer or a molecule able to react with an element likely to be present in the sample can be mentioned. By "molecule able to react with an analyte of interest", it is meant either a molecule in particular of the enzyme type able to transform this element into another compound or to obtain from this element another compound, or a molecule in particular of the antibody type able to form with an analyte of interest a complex or binding pair. This chemical reagent can be present, in the device according to the invention, prior to taking, in particular in dry form in the tank, in the porous matrix and/or on the porous matrix.

Alternatively, this chemical reagent can be brought in the device after taking the sample. In this case, once the sample is in the tank, it is possible to disconnect the plug/piston from the enclosure and to deposit this reagent onto the porous matrix before reconnecting the plug to the enclosure and to bring it back to the final position whereby the chemical reagent passes through the porous matrix and is placed in the tank in the presence of the sample.

In another alternative implementing both a porous matrix in the form of a filtration membrane and a chemical reagent, it is possible that the sample is initially treated by the filtration membrane so as to retain elements of interest at the filtration membrane. This treatment consists in filtering the sample; the latter can be performed via compressing the sample by bringing the plug/piston back to the final position and/or via sucking the sample. In the latter case, a depression can be made at the second end of the enclosure, in particular by connecting the hole present at this end to a vacuum pump or a syringe. Following this filtration, the elements of the sample which have not been retained by the filtration membrane can be removed in particular by replacing the tank containing them with another tank. Then, the plug is disconnected from the enclosure. The chemical reagent is then deposited onto the porous matrix before reconnecting the plug to the enclosure and bringing it back to the final position, whereby the chemical reagent is in contact with the elements of interest retained at the filtration membrane and then the reaction products between these elements and the chemical reagent pass into the tank as illustrated in the example IV.2.a hereinafter.

The fact that the sample can be directly treated in the device according to the invention has many advantages. First, this treatment does not require any manipulation by a third party after it has been taken; the reproducibility and reliability of the analyses are enhanced thereby. Moreover, since the treatment occurs in the device, the contact times between the sample and the chemical reagents are longer than the contact times on conventional strip tests, which participates in increasing the signal detected.

It is to be noted that the materials used for manufacturing the device for taking and optionally treatment according to the invention and in particular used for the parts likely to be in contact with the sample have a low interaction and are typically chosen so as not to interact with the analyte(s) of interest to be studied in order to minimise sorption and desorption problems on the exchange surfaces provided by the device.

The present invention also relates to a system for detecting and optionally quantifying an analyte of interest likely to be present in a sample, the system comprising:

a cassette having an aperture, at least one strip able to receive said sample via said aperture and having a visual indicator indicating the presence of an analyte of interest in said sample being placed in said cassette and a device as previously defined and in particular the tank of which has an occludable hole, said device being in fluid connection with the cassette through the occludable hole switching from a closed configuration to an open configuration in response to the connection of the aperture of the cassette with the occludable hole of the device.

In such a system, the deposition of the sample at the cassette is facilitated.

The analyte to be detected and optionally to be quantified is present in the liquid or surface sample prior to taking or is in this sample following its treatment in the device according to the invention. The analyte to be detected can be chosen from the group consisting of a molecule of biologic interest; a molecule of pharmacological interest; a toxin; a peptide; a protein; a glycoprotein; an enzyme; an enzymatic substrate; a nuclear or membrane receptor; an agonist or antagonist of a nuclear or membrane receptor; a hormone; a polyclonal or monoclonal antibody; an antibody fragment such as a fragment Fab, $F(ab')_2$, Fv or a hypervariable domain or CDR ("Complementarity Determining Region"); a bacterium and a virus. Depending on the analyte to be detected, those skilled in the art will be able to determine, without inventive effort, the labelled compounds and non-labelled compounds to be used to achieve a visual indication at the cassette when this analyte is present in the sample studied.

A cassette in which at least one strip able to receive a sample and having a visual indicator indicating the presence of an analyte of interest in this sample is placed is known per se in the field of detection and optional quantification of an analyte of interest. The originality of this cassette within the scope of the present invention resides in the fact that it has an aperture adapted to be connected to the occludable hole of the tank of the device containing the sample and enable this hole to be opened and hence the sample to be introduced in the cassette. Thus, when the occludable hole is occluded by a breakable occluder having a spike, the connection of the device to the cassette causes the compression of the spike linked to the breakable occluder which causes the hole to open. Actually, opening the hole is controlled and can only occur when the device is connected to the cassette. This feature secures deposition of the sample by avoiding any overflow or deposition risk apart from the use of the cassette having the aperture adapted to the occludable hole of the tank.

Any means for removably connecting the aperture of the cassette to the occludable hole of the tank of the device is usable within the scope of the present invention. By way of illustrating examples, this connection can involve screwing, clipping, notching, ribbing and/or bayonet attachment. In one advantageous embodiment, this connection is made by screwing and the aperture of the cassette is connectable to the hole of the tank of the device by means of threads.

Since a large amount of samples can be introduced in the cassette because of the device and the inner volume of the tank used to take this sample, the cassette implemented can be configured to test different analytes of interest without a sensitivity loss. To that end, this cassette comprises several strips and in particular two, three, four, five or more strips.

The present invention finally relates to a kit of parts comprising both elements forming the analysis system as previously described, in a form disconnected from each other and the hole of the device which participates in this connection is protected by a plug, the aperture of the cassette being in turn optionally protected or not by a plug. In other words, the present invention relates to a kit of parts comprising:

a cassette having an aperture optionally protected by a plug and at least one strip able to receive said sample via said aperture and having a visual indicator indicating the presence of an analyte of interest in said sample being placed in said cassette and a device as previously defined and in particular the tank of which has an occludable hole protected by a plug.

Further characteristics and advantages of the present invention will further appear to those skilled in the art upon reading the examples below given by way of illustrating and in no way limiting purposes, in reference to the appended figures.

BRIEF DESCRIPTION OF THE DRAWINGS

FIG. 1 relates to the first module of the device for taking and optionally treating according to the present invention.

FIG. 2 relates to the second module of the device for taking and optionally treating according to the present invention.

FIG. 3 relates to the third module of the device for taking and optionally treating according to the present invention.

FIG. 4 provides longitudinal cross-section partial schematic representations of the device according to the invention in use. FIGS. 4A, 4B and 4C correspond to the device before taking or just after taking, to the device in which the plug/piston is in the so-called "initial position" and to the device in which the plug/piston is in the so-called "final position".

FIG. 5 provides longitudinal cross-section partial schematic representations of the device according to the invention in which the occluder not protected (FIG. 5A) or protected by a plug (FIG. 5B) is adapted to a use of this device in an analysis system according to the invention. FIG. 5C is an alternative of FIG. 5B in which the tank and the enclosure form a single structure.

FIG. 7 is a sequential series of longitudinal cross-section partial schematic representations of the device according to the invention upon connecting the same to a cassette as implemented in the analysis system according to the invention.

FIG. 8 is a comparison of the signal obtained with an analysis system according to the invention or with a conventional strip test type cassette for different concentrations of botulinum toxin.

FIG. 9 provides longitudinal cross-section partial schematic representations of alternatives of the device according to the invention.

DETAILED DISCLOSURE OF PARTICULAR EMBODIMENTS

I. Device According to the Invention.
I.1. Description.

In what follows, the term "radial" is defined with respect to the axis AA' of the device according to the invention 1.

Figure 1A:
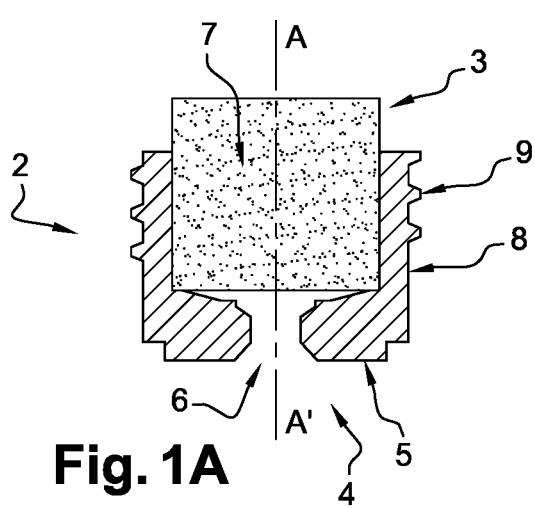
FIG. 1A is a longitudinal cross-section partial schematic view of the first module of the device for taking and optionally treating according to the present invention.
Figure 1B:
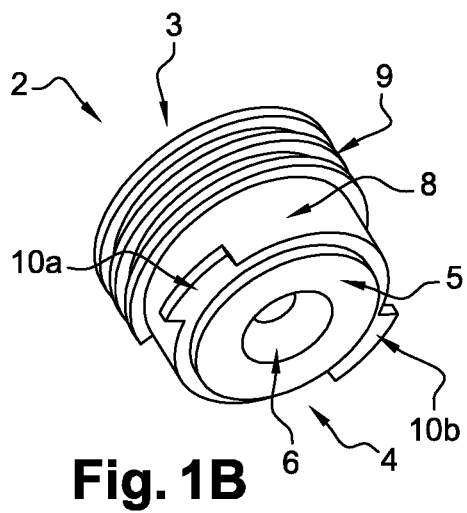
FIG. 1B is a perspective partial schematic view of the first module of the device for taking and optionally treating according to the present invention.

FIGS. 1A and 1B represent the first module of the device for taking and optionally treating according to the invention. This first module is in the form of an enclosure 2 corresponding to a plastic (photopolymerisable resin, 3D printing), 1.3 cm high, circular cross-section tubular cylindrical part having a first open end 3 and a second end 4, said ends being positioned facing each other. This second end is closed by a wall 5 pierced with a single hole 6. Inside the cylinder forming the enclosure, a sponge or foam type, porous compressible matrix 7 is located. The porous compressible matrix 7 has a circular cross-section solid cylindrical shape and its diameter is identical or substantially identical to the internal diameter of the tubular cylindrical shaped enclosure. In the absence of any element connected to the first open end 3, the porous compressible matrix 7 slightly projects from this aperture. Finally, in order to connect this first module to the second module and to the third module of the device according to the invention, the external surface 8 of the cylinder forming the enclosure has, in a top part, i.e. on the side of the first end 3, a thread or screw pitch 9 enabling the second module to be screwed, and at a bottom part i.e. on the side of the second end 4, lugs (or protrusions) 10a and 10b for connection to the third module.

Figure 2A:
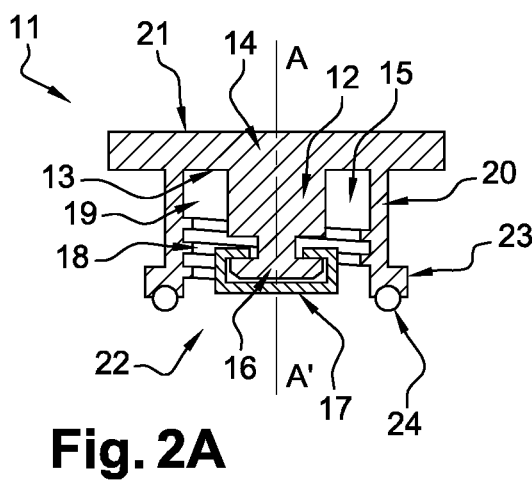
FIG. 2A is a longitudinal cross-section partial schematic view of the second module of the device for taking and optionally treating according to the present invention.
Figure 2B:
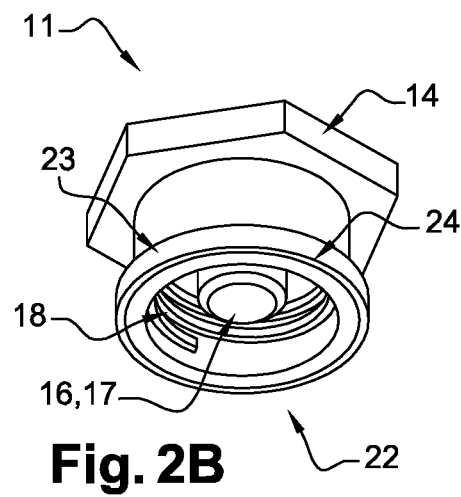
FIG. 2B is a perspective partial schematic view of the second module of the device for taking and optionally treating according to the present invention.

FIGS. 2A and 2B represent the second module of the device for taking and optionally treating according to the invention. This second module corresponds to a plug/piston 11. The piston 12 of this module is in the form of a single circular cross-section closed cylinder, 1.7 cm high, mounted, i.e. attached to the inner face 13 of the closed end 14 of the plug and extending in the cavity of the plug 15. The head of the piston 16 has a rubber type flexible material 17 acting as a seal, this material covering the piston head and extending circumferentially about the same. Since the plug/piston 11 is connected to the first end 3 of the enclosure by screwing, a thread or screw pitch 18 is provided inside the cavity 15 of the plug, on the internal surface 19 of the sidewall 20. Thus, the thread 18 enables the first module 2 to be assembled with the second module 11 by screwing on the corresponding thread 9 provided on the external surface 8 of the cylinder forming the enclosure. In this embodiment, the piston and the plug have the same axis of rotation corresponding to the axis AA'. The external face 21 of the closed end of the plug 14 enables information about the collected sample to be written therein. The plug has, facing its closed end 14, an open end 22. At this open end 22, the sidewall 20 has a radially projecting shoulder 23. This shoulder 23 carries a seal 24 such as an O-ring seal. The different elements forming this second module and in particular the closed end 14, the sidewall 20 and the piston 11 are of plastic (photopolymerisable resin, 3D printing).

Figure 3A:
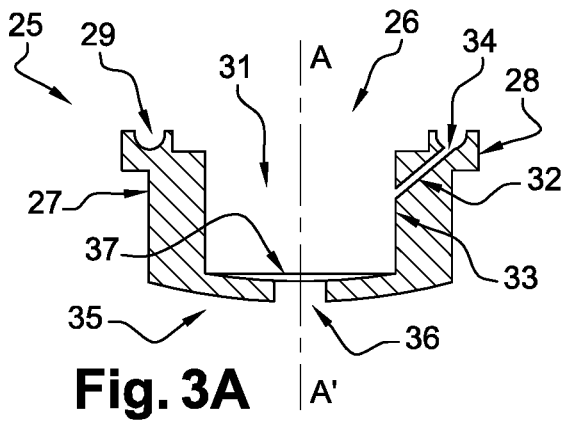
FIG. 3A is a longitudinal cross-section partial schematic view of the third module of the device for taking and optionally treating according to the present invention.
Figure 3B:
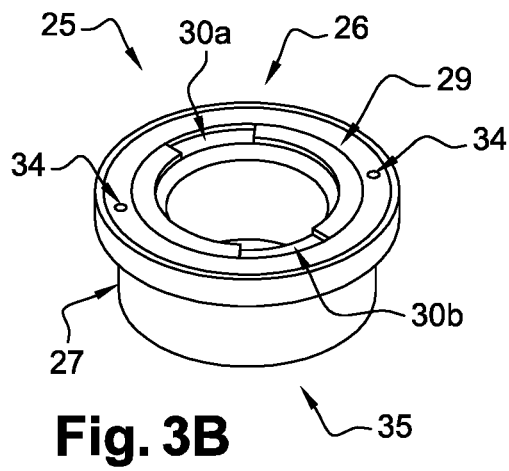
FIG. 3B is a perspective partial schematic view of the third module of the device for taking and optionally treating according to the present invention.
Figure 6A:
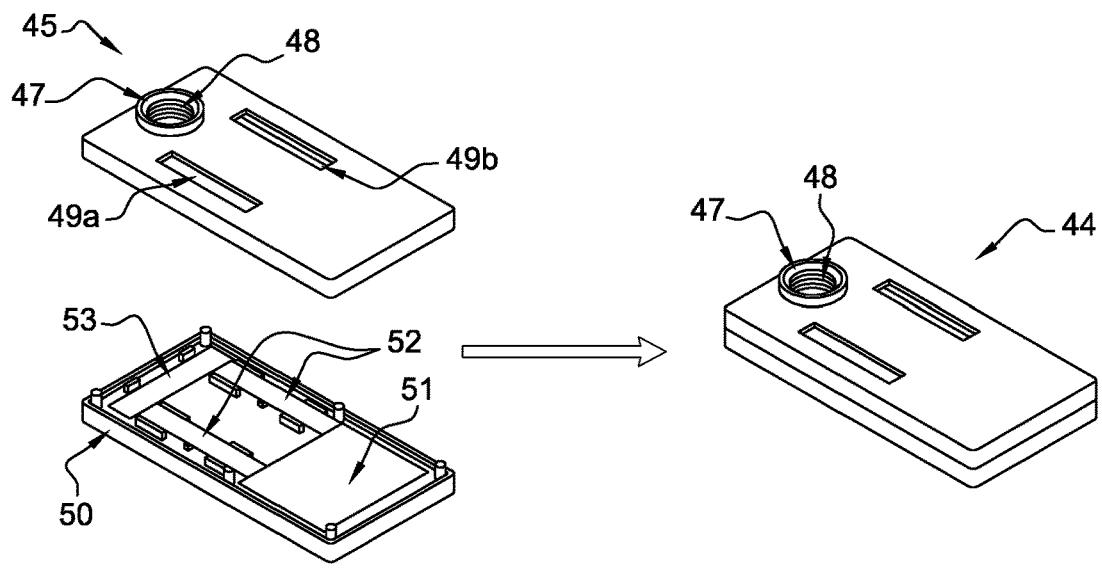
FIG. 6 shows different cassettes usable in the analysis system according to the invention, the latter comprising two strips (FIG. 6A), a single strip (FIG. 6B) or four strips (FIG. 6C).
Figure 6A:
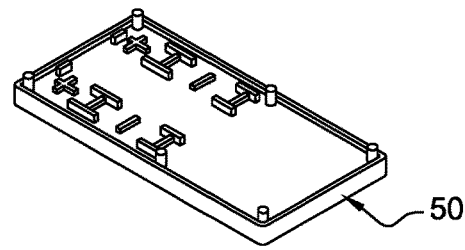
Figure 6B:
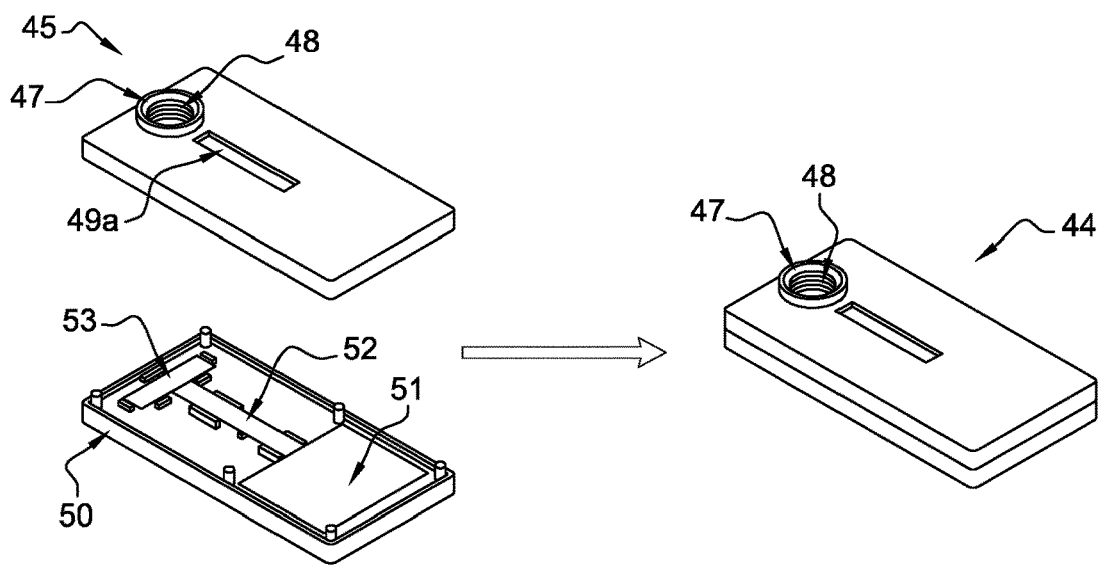
Figure 6B:
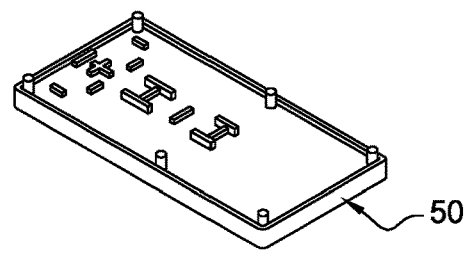

FIGS. 3A and 3B represent the third module of the device for taking and optionally treating according to the invention. This third module is in the form of a circular cross-section tubular cylindrical shaped tank 25, 1.3 cm high, with a first open end 26. This first open end 26 directly participates in connecting the enclosure 2. At the first open end 26, the external diameter of the tank 25 is higher than the external diameter of the enclosure 2. The sidewall 27 of the tank 25 has, at this open end 26, a radially projecting shoulder 28. The external diameter of this shoulder 28 is identical or substantially identical to the external diameter of the shoulder 23 of the plug/piston 11. Moreover, the shoulder 28 has a hemispherical cavity or throat 29 wherein the seal 24 carried by the shoulder 23 can be sealingly housed. This shoulder 28 has also notches 30a and 30b which participate with the lugs 10a and 10b in assembling the third module with the first module by notching or drawing stamping. The inside or internal volume 31 of the tank is connected to the outside by one or more conduits 32. This(these) conduit(s) 32 is/are connected at the inner surface 33 of the sidewall 27 of the tank 25 and open(s) at one or more hole(s) 34 present at the shoulder 28 and more particularly at the hemispherical cavity or throat 29. Finally, facing with the first open end 26, there is a wall or second end 35 pierced with a hole 36 occluded by an occlude 37.

I.2. Operation.

A. Taking of a Liquid Sample.

The liquid sample is deposited onto the porous compressible matrix 7 which absorbs the same (FIG. 4A). After the sample is recovered, the plug/piston 11 is screwed to the enclosure 2 via the threads 9 and 18 whereby the plug/piston is in the so-called "initial position" (FIG. 4B). By sinking in the enclosure 2, the piston 12 compresses the porous compressible matrix 7 which causes the sample to be transferred into the tank 25. The overpressure in the tank is avoided thanks to the conduits 32 which enable air to be expelled outside. Screwing the plug/piston 11 to the enclosure 2 is made until the O-ring seal 24 is fully inserted in the hemispherical cavity or throat 29, whereby the plug/piston is in the so-called "final position" (FIG. 4C). The insertion of the seal 24 in the cavity 29 hermetically closes the conduits 32. At the end of the operation (FIG. 4C), the sample is hermetically contained in the tank 25 and elements could have been added or removed. The tank 25 and the plug/piston 11 are sealingly coupled to each other, creating a sealed closed inner volume 38 in which the enclosure 2 is located. The sample could thereby be stored or transported in a secured way. A friable adhesive tape not represented can be disposed at the joint 39 between the plug/piston 11 and the tank 25 to ensure the device is not opened between taking the sample and analysing it.

B. Taking a Surface Sample.

A buffer solution is deposited onto the porous compressible matrix 7 which absorbs the same. The surface on which the presence of the substance desired to be analysed is suspected is rubbed with the end of the porous compressible matrix 7 which projects from the enclosure 2. The plug/piston 11 is screwed to the enclosure 2 and then the following of the operations is similar to that described for a liquid sample.

II. Analysis System According to the Present Invention.

For the use of a device 1 according to the invention in an analysis system with a cassette and strip tests, the occlude 37 of the tank 25 is linked to a spike 40 which is surrounded by a small cylinder 41 attached to the outer face 42 of the bottom of the tank 25. On the outer face of this cylinder 41, a screw pitch or thread 43 (FIG. 5A) which enables the tank 25 to be screwed to the upper part 45 of a strip cassette 44 has been made. For the spike 40 not to be broken during taking or storing the sample, a protective plug 46 is screwed to the cylinder surrounding it (FIG. 5B). FIG. 5C is an alternative of FIG. 5B in which the tank is irremovably connected to the second end of the enclosure, the tank and the enclosure forming a single structure.

After taking the sample and transferring it by screwing the plug/piston 11 in the tank 25, this could be deposited on strip(s) when the manipulator desires it. To facilitate this operation, the analysis system according to the invention implements particular cassettes. Indeed, they have an aperture 47 for the deposition with a screw pitch 48 which corresponds to the screw pitch 43 of the cylinder 41 surrounding the spike 40 linked to the occlude 37 of the tank 25.

The other elements of these cassettes 44 are the same as those present in the cassettes of the state of the art (FIG. 6). Consequently, there are also, in the cassettes 44 of the invention, a cap-forming upper part 45 comprising, in addition to the previously described aperture 47, result reading windows 49a, 49b, 49c and 49d, and a lower part 50 where the strip(s) formed with 3 zones attached together on a plastic support are located, with (i) an absorption zone 51 promoting migration, (ii) a reaction zone 52, generally formed by a nitrocellulose membrane and (iii) a deposition zone 53 receiving the sample.

By way of examples, the cassettes 44 implemented in the analysis system according to the invention can allow the use of two strips simultaneously (FIG. 6A), of a single strip (FIG. 6B) or four strips simultaneously (FIG. 6C) can also be used.

Figures 6C, 7, 8:
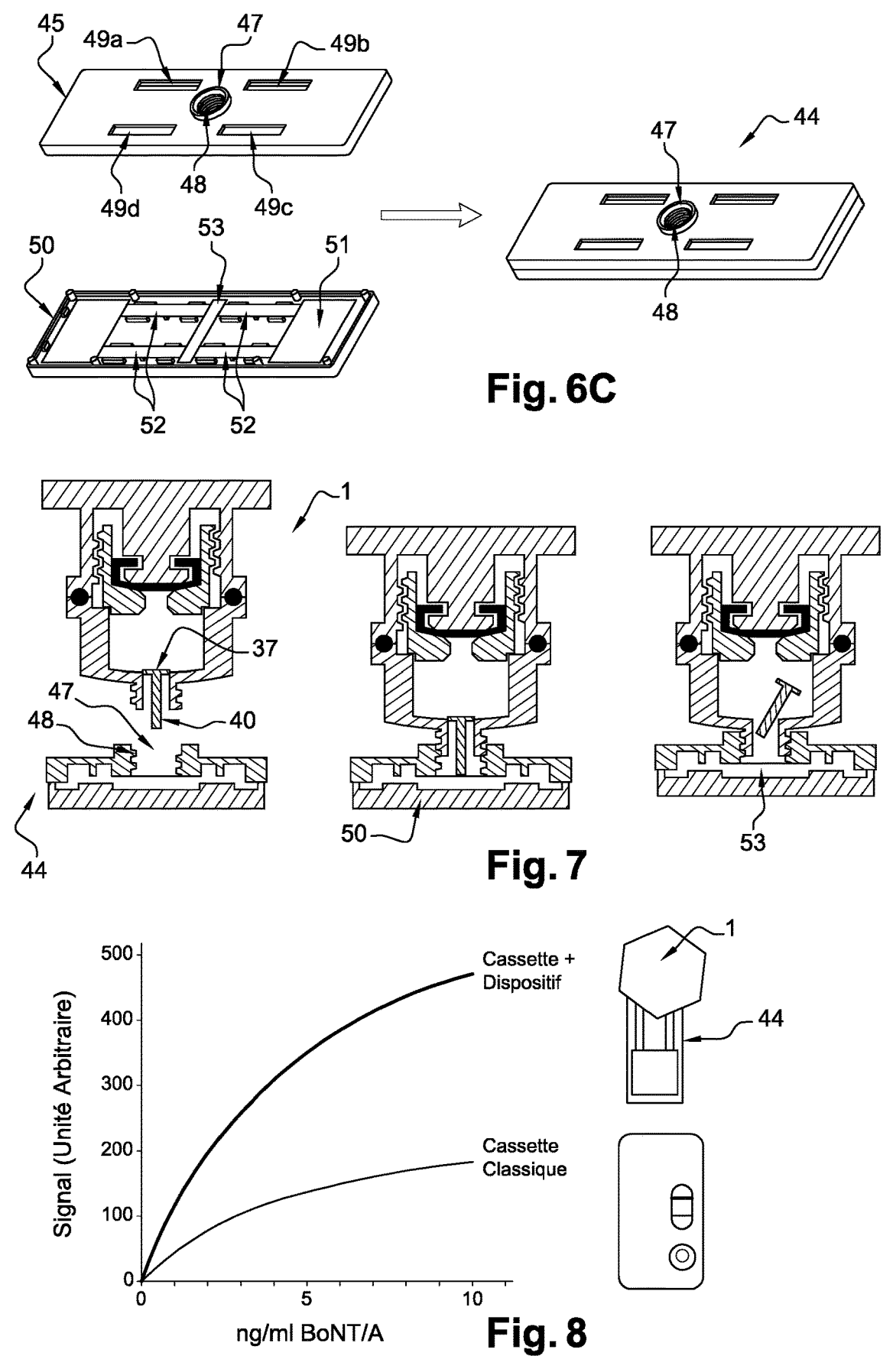

For depositing the sample on the analysis system according to the invention, the manipulator has to unscrew the protective plug 46 and screw the device 1 to the cassette 44. In doing so, it compresses the spike 40 against the bottom part 50 of the cassette 44 and thus detaches the occlude 37 from the bottom of the tank 25 which triggers depositing the sample onto the deposition zone 53 of the strip (FIG. 7).

III. Validation of the Device and Analysis System According to the Invention.

All the validation experiments have been made with strips for detecting botulinum toxin A.

III.1. Recovery Rate of a Liquid or Surface Sample with the Device.

A. Material and Method.

The strip buffer has the following composition: 0.1 M Tris/HCl buffer pH 8+0.15 M NaCl+0.5% Tween 20+1% Chaps+0.01% sodium azide.

The EIA buffer has the following composition: 0.1 M potassium phosphate buffer pH 7.4+0.1% BSA+0.15 M NaCl+0.01% sodium azide.

4 ml of 3 ng/ml botulinum toxin are prepared in the EIA buffer. One ml of this solution is deposited into two plastic cups and allowed to dry for 24 h under a hood.

The content of a cup is recovered with 1 ml of strip buffer. One hundred µl of this solution are taken (sample A) and 900 µl are deposited onto the porous material of the device and then recovered at the outlet of the tank after using the device (sample B).

One ml of strip buffer is deposited onto the porous material of the device. The content of the $2^{nd}$ cup is recovered by rubbing the surface of the cup with the porous material. After using the device, the solution is recovered at the outlet of the tank (sample C). Nine hundred µl of the botulinum toxin solution are directly deposited onto the device. This solution is recovered at the outlet of the tank after using the device (sample E). The solution of botulinum toxin A (sample D) as well as the other samples are assayed by immunological assay.

B. Results.

The immunological assay results are given in table 1 hereinafter as a function of the sample.

TABLE 1

| Samples | Concentration |
|---------|---------------|
| A | 2.4 ng/ml |
| B | 2.4 ng/ml |
| C | 1.8 ng/ml |
| D | 3.4 ng/ml |
| E | 3.4 ng/ml |

The recovery rate of a liquid sample after using the device corresponds to: (D/E)×100 and (B/A)×100. A 100% rate is obtained for both measurements. The recovery rate of a surface sample corresponds to: (C/E)×100, that is 53%. This value is close to that obtained by re-solubilising the sample (A/E)×100: 70%.

C. Analysis.

This experiment shows that the device enables a liquid sample to be treated without any loss.

On the other hand, it is shown that the device enables 53% of a surface sample to be recovered. The rate obtained by re-solubilising the sample shows that it is difficult to recover the entire sample dried on a surface (70%). Indeed, a more or less important part of the molecules of this sample, depending on the nature of the sample and the surface, is absorbed on the same and is no longer available for analysis.

III.2. Comparison Between Conventional Strip-Test and Analysis System According to the Invention.

A. Protocol.

In this study, the same strips are used in both formats. However, for tests using the device according to the invention, the tracer antibody is dried on a glass fibre membrane which is placed between the porous material and the bottom of the collector. For conventional tests, this tracer antibody is dried on a glass fibre membrane placed between the deposition zone and the detection zone (position used in commercial tests). For each device, 1 ml of strip buffer is dried in the porous material.

For conventional tests, cassettes containing a strip with a deposition hole without a screw pitch are used. For tests using the device according to the invention, cassettes containing 2 strips (FIG. 6A) and with a hole with a screw pitch, are used according to the previously described protocol.

For conventional tests, 100 µl of sample are deposited. For tests using the device according to the invention, 1 ml of sample is deposited onto the porous material and the sample is stored for 5 min in the tank before deposition onto the cassette.

Solutions are deposited with different botulinum toxin A concentrations (0; 0.3; 1; 3 and 10 ng/m). The signals obtained at the test line are read with a strip reader (Qiagen).

B. Results.

The signals obtained via a strip reader (Qiagen) expressed as arbitrary units are shown in FIG. 8.

C. Analysis.

In FIG. 8, it is observed that the use of the device and the analysis system according to the invention enables the signals obtained at the test line to be strongly increased for a same concentration in comparison with the signals obtained with a conventional test.

III.3. Influence of the Distance Between the Deposition Zone and the Test Line.

Within the scope of multiplex detection (several targets detected simultaneously) on a same strip, it is necessary to make several test lines. These different lines thus will not be at the same distance to the deposition zone.

For conventional tests, the tracer antibody is located after the deposition zone, the contact time between the tracer antibody and the sample before reaching the test line will thus be a function of the distance of the same with respect to the deposition zone. In this experiment, the distances indicated correspond to the distance between the beginning of the detection zone and the test line.

A. Protocol.

Strips are prepared with test lines at different distances from the beginning of the detection zone. The tracers are prepared as for the previous experiment. For conventional tests, cassettes containing a strip with a deposition hole without a screw pitch are used. For tests with the device according to the invention, cassettes containing 2 strips (FIG. 6A) and with a hole with a screw pitch are used. The test is performed according to the previously described protocol.

For conventional tests, 100 µl of sample are deposited and two tests are made for each distance. For tests with the device, 1 ml of sample is deposited onto the porous material and the sample is stored for 5 minutes in the tank before deposition onto the cassette.

3 ng/ml botulinum toxin solutions are deposited. The signals obtained at the test line are read with a strip reader (Qiagen).

B. Results.

The signals obtained via a strip reader (Qiagen) expressed as arbitrary units are shown in table 2 below.

TABLE 2

| | Conventional cassette | | Cassette with the device according to the invention | |
|---|---|---|---|---|
| Distance (d) | Strip 1 | Strip 2 | Strip a | Strip 2 |
| 5 mm | 39 | 58 | 304 | 338 |
| 13 mm | 120 | 102 | 355 | 297 |
| 17 mm | 144 | 112 | 332 | 328 |

C. Analysis.

In table 2, it is observed that the signals obtained with the conventional tests increase with an increasing distance between the test line and the deposition zone. Unlike tests performed with the device according to the invention for which the signals remain identical regardless of the distance from the test line. Thus, the homogeneity of the signals whatever the distance between the deposition and the test line enables multiplex test to be made without a signal loss and thus a sensitivity loss.

On the other hand, it is noticed for tests with the device according to the invention that the values of the signals are identical on strips 1 and 2 contents in the same cassette, which demonstrates that the sample is equally distributed and both strips upon migration.

This experiment also confirms the results shown in point II.2.C showing that the signals obtained with the device are higher than those obtained with a conventional test.

D. Conclusion.

The device according to the invention enables a liquid or surface sample to be simply collected with a good recovery rate. It enables the same to be stored and securely transported. On the other hand, its association with cassettes for adapted strips enables signals obtained to be increased and allows the development of multiplex test without a sensitivity loss. It also enables the sample to be deposited on the strip(s) without pipetting.

IV. Exemplary Use of the Device and the Analysis System According to the Invention for Detecting Antibiotic-Resistance Enzymes.

IV.1. Modifications of the Device According to the Invention.

Figure 9A:
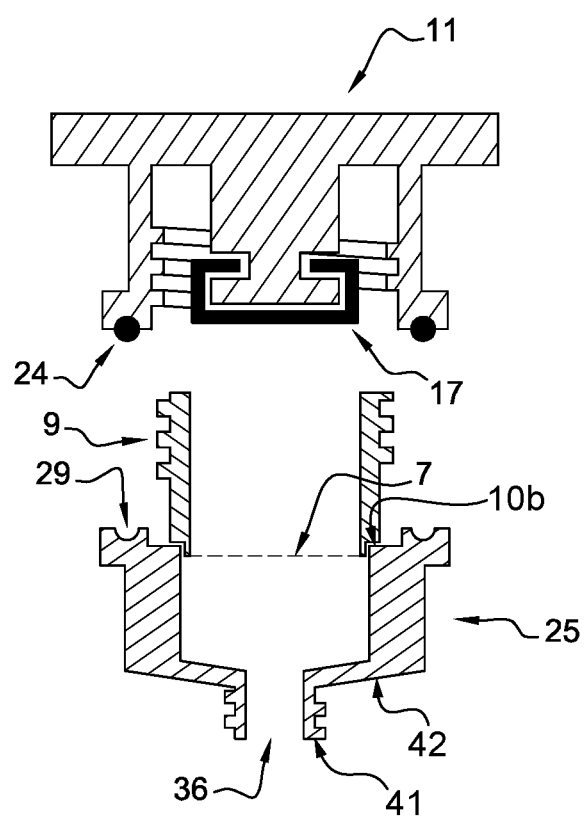
FIGS. 9A and 9B correspond to a device according to the invention in which the porous matrix is in the form of a filtration membrane with a tank the occludable hole of which is in non-occluded position (FIG. 9A) or with a tank the occludable hole of which is occluded by an occluder with a spike (FIG. 9B).
Figure 9B:
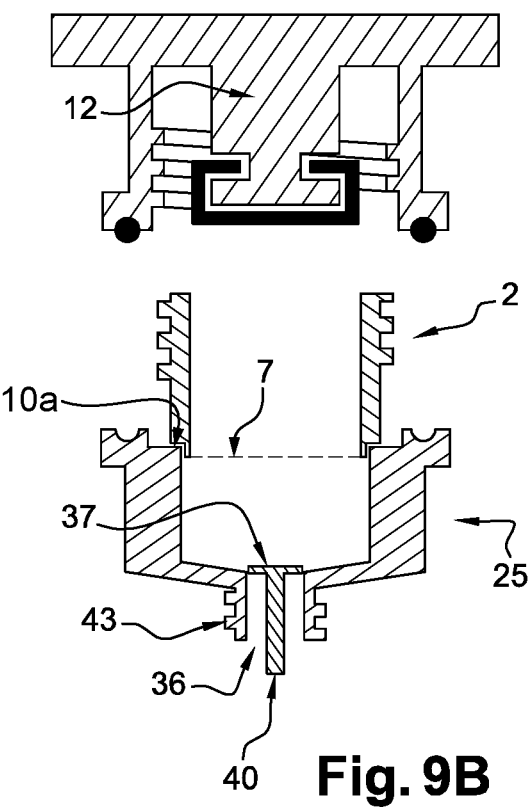

For this example, the porous matrix 7 is a 0.45 μm filtration membrane inserted at the bottom of the enclosure 2 the second end 4 of which has an internal diameter equal to the diameter of the hole 6. The link between the enclosure 2 and the tank 25 is made thanks to a system of lugs 10a and 10b which allows them to be separated at will. Two types of tanks 25 are used: a tank 25 the hole 36 of which is open, i.e. without an occlude (FIG. 9A) and a tank 25 the hole 36 of which is closed by an occlude 37 linked to a spike 40 which is surrounded by a small cylinder 41 attached to the outer face 42 of the bottom of the tank 25 (FIG. 9B).

IV.2. Protocol.

A. Material.

To perform the following experiments, *Escherichia coli* type bacteria are used, which produce antibiotic-resistance enzymes (beta-lactamase) CTXM and which are cultured in LB medium with an antibiotic, 100 μg/ml ampicillin.

B. Method.

For this utilisation, 1 ml of liquid sample containing *Escherichia coli* culture medium supplemented with 100 μg/ml ampicillin) is deposited in the sampler. The bottom of the sampler is occluded using a plug or a pressure sensitive adhesive plastic film. The upper part of the sampler is occluded with a plug, a pressure sensitive adhesive plastic film or another system.

The sampler is incubated at 37° C. under stirring for a determined duration and then is opened at both ends and linked to the open tank. The plug/piston is screwed to the sampler which induces filtration of the sample through the 0.45 μm filter. The bacteria contained in the sample remain at the sampler whereas the rest of the sample (structures with a diameter lower than 0.45 μm) is removed via the open tank.

The plug/piston is unscrewed and the open tank is replaced with the occluded tank in which the tracer antibody (ies) has/have been dried. In the sampler, 500 μl of a solution enabling the bacterial beta-lactamases to be extracted are deposited. The piston plug is again screwed to the sampler which causes the extraction solution containing the beta-lactamases to pass through the tank. The beta-lactamase detection is made by screwing the device on an adapted cassette dedicated to the detection of these beta-lactamases.

IV.3. Results.

Without incubation, the detection limit of resistant *Escherichia coli* is $10^6$ Colony Forming Units per ml (CFU/ml). After two hours of incubation in the enclosure of the device, i.e. after two hours of contact between the beta-lactamases and the tracer antibody(ies), this detection limit is $10^4$ CFU/ml and after four hours of incubation, this detection limit is $10^2$ CFU/ml.

REFERENCES

[1] International application WO 2012/118392 on behalf of Infogene Lda, published on 7 Sep. 2012.
[2] International application WO 2008/030817 on behalf of Yong, published on 13 Mar. 2008.
[3] International application WO 95/08761 on behalf of Polyfiltronics, Inc., published on 30 Mar. 1995.
[4] International application WO 2009/036168 on behalf of University of Florida Research Foundation, Inc., published on 19 Mar. 2009.
[5] International application WO 2009/153559 on behalf of the Secretary of State for Defence, published on 23 Dec. 2009.
[6] Patent application US 2016/121322 on behalf of Premier Biotech, Inc., published on 5 May 2016.

The invention claimed is:

1. A device for taking a sample, comprising:
   an enclosure with a first open end and a second end having a hole,
   a porous matrix, disposed in said enclosure and able to recover said sample, wherein said porous matrix is either compressible or not compressible,
   a plug connectable to said first end of said enclosure and having a piston sealingly closing said first end of said enclosure, said plug being movable with respect to said enclosure from an initial position to a final position whereby said piston contacts a top edge of said porous matrix to compress said porous matrix when said porous matrix is compressible or whereby said piston compresses said sample when said porous matrix is not compressible,
   a tank connectable to said second end of said enclosure such that, when said porous matrix is compressible, a bottom edge of said porous matrix is positioned above a top edge of the tank when said tank is in direct contact with the second end of said enclosure, and said tank is in fluid connection with said enclosure via said hole so as to recover the sample restored by said porous matrix under the effect of the compression of said porous matrix or said sample by said piston, said tank having one or more conduit(s) connecting the inner volume of the tank to the outside,
   sealing means being present between a bottommost edge of said plug and an uppermost edge of said tank, and
   wherein, when said plug and said tank are connected to said enclosure and when said plug is in said final position, said plug is in direct contact with said tank to sealingly close said tank and occlude said conduit(s).

2. The device according to claim 1, wherein, when said plug and said tank are connected to said enclosure and when said plug is in the final position, said plug and said tank form a single sealed closed volume which contains said enclosure.

3. The device according to claim 1, wherein said sealing means are in the form of a seal carried by the plug.

4. The device according to claim 1, wherein said plug is connectable to said first end of said enclosure by threads.

5. The device according to claim 1, wherein when said porous matrix is compressible, said porous matrix is in the form of a sponge, a foam, or a pad.

6. The device according to claim 1, wherein when said porous matrix is not compressible, said porous matrix is a filtration membrane.

7. The device according to claim 1, wherein said tank has a hole that is occludable by a removable occluder.

8. The device according to claim 7, wherein said device has a plug to protect said occludable hole.

9. The device according to claim 1, wherein said device further comprises at least one element to physically or chemically process said sample.

10. The device according to claim 9, wherein said at least one element is a filtration membrane.

11. The device according to claim 9, wherein said at least one element is a chemical reagent.

12. A system for detecting an analyte of interest likely to be present in a sample, the system comprising:

a cassette having an aperture, at least one strip to receive said sample via said aperture and having a visual indicator indicating the presence of an analyte of interest in said sample being placed in said cassette, and the device according to claim 7 in fluid connection with the cassette through the occludable hole switching from a closed configuration to an open configuration in response to the connection of said aperture of said cassette with said occludable hole of said device.

13. The system according to claim 12, wherein the connection of the aperture of said cassette with the occludable hole of said device is made by screwing.

14. The system according to claim 12, wherein said cassette comprises several strips.

15. A kit of parts comprising:

a cassette having an aperture and at least one strip to receive said sample via said aperture and having a visual indicator indicating the presence of an analyte of interest in said sample being placed in said cassette, and the device as defined in claim 8.

16. The kit according to claim 15, wherein the aperture of the cassette is protected by a plug.

17. The device according to claim 1, wherein the uppermost edge of said tank includes a hemispherical cavity to receive a seal of the sealing means.

18. The device according to claim 17, wherein each of said conduit(s) includes a first opening at an inner surface of a sidewall of the tank and a second opening in the hemispherical cavity.

19. The device according to claim 3, wherein the seal is positioned below a bottommost face of the piston.

* * * * *